US011155575B2

(12) United States Patent
Iyer et al.

(10) Patent No.: US 11,155,575 B2
(45) Date of Patent: Oct. 26, 2021

(54) NON-ANTIBODY HIGH-AFFINITY-BASED SAMPLE PREPARATION, SORBENT, DEVICES AND METHODS

(71) Applicant: WATERS TECHNOLOGIES CORPORATION, Milford, MA (US)

(72) Inventors: Laks Iyer, Hudson, MA (US); Beatrice W. Muriithi, Attleboro, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 16/360,265

(22) Filed: Mar. 21, 2019

(65) Prior Publication Data

US 2019/0292222 A1    Sep. 26, 2019

Related U.S. Application Data

(60) Provisional application No. 62/646,277, filed on Mar. 21, 2018.

(51) Int. Cl.
| | | |
|---|---|---|
| *C07K 1/30* | (2006.01) | |
| *C07K 1/36* | (2006.01) | |
| *G01N 33/53* | (2006.01) | |
| *C07K 1/22* | (2006.01) | |

(52) U.S. Cl.
CPC .............. *C07K 1/30* (2013.01); *C07K 1/36* (2013.01); *G01N 33/5308* (2013.01); *C07K 1/22* (2013.01)

(58) Field of Classification Search
None
See application file for complete search history.

(56) References Cited

U.S. PATENT DOCUMENTS

| | | | |
|---|---|---|---|
| 4,560,647 A | 12/1985 | Stocker | |
| 4,639,513 A | 1/1987 | Hou et al. | |
| 4,704,366 A | 11/1987 | Juarez-Salinas et al. | |
| 5,075,423 A | 12/1991 | Balint, Jr. | |
| 5,422,284 A | 6/1995 | Lau | |
| 5,429,746 A | 7/1995 | Shadle et al. | |
| 5,449,461 A | 9/1995 | Ito | |
| 5,935,780 A | 8/1999 | Naser | |
| 6,013,457 A | 1/2000 | Neuenhofer et al. | |
| 6,030,770 A | 2/2000 | Brust | |
| 6,139,746 A | 10/2000 | Kopf | |
| 6,258,551 B1 | 7/2001 | Neuenhofer et al. | |
| 6,444,461 B1 | 9/2002 | Knapp et al. | |
| 6,459,994 B1 | 10/2002 | Parekh et al. | |
| 6,797,523 B2 | 9/2004 | Awrey et al. | |
| 6,946,075 B2 | 9/2005 | Kopf | |
| 7,083,948 B1 | 8/2006 | Sassenfeld et al. | |
| 7,179,655 B2 | 2/2007 | Patricelli | |
| 7,198,896 B2 | 4/2007 | Rush et al. | |
| 7,220,356 B2 | 5/2007 | Thommes et al. | |
| 7,300,753 B2 | 11/2007 | Rush et al. | |
| RE40,070 E | 2/2008 | Shadle et al. | |
| 7,332,289 B2 | 2/2008 | Takeda et al. | |
| 7,385,040 B2 | 6/2008 | Johansson et al. | |
| 7,405,083 B2 | 7/2008 | Chen | |
| 7,524,641 B2 | 4/2009 | Jurgensen et al. | |
| 7,662,930 B2 | 2/2010 | Zhou | |
| RE41,555 E | 8/2010 | Shadle et al. | |
| RE41,595 E | 8/2010 | Shandle et al. | |
| 7,790,040 B2 | 9/2010 | Mierendorf et al. | |
| 7,820,799 B2 | 10/2010 | Godavarti et al. | |
| 7,825,223 B2 | 11/2010 | Godavarti et al. | |
| 7,847,071 B2 | 12/2010 | Bonnerjea et al. | |
| 7,875,462 B2 | 1/2011 | Gjerde et al. | |
| 7,888,134 B2 | 2/2011 | Zeng et al. | |
| 8,057,668 B2 | 11/2011 | Gjerde et al. | |
| 8,067,182 B2 | 11/2011 | Kelley et al. | |
| 8,084,032 B2 | 12/2011 | Yumioka et al. | |
| 8,137,561 B2 | 3/2012 | Kozlov et al. | |
| 8,143,071 B2 | 3/2012 | Gjerde | |
| 8,148,168 B2 | 4/2012 | Gjerde et al. | |
| 8,192,942 B2 | 6/2012 | Koo et al. | |
| 8,263,343 B2 | 9/2012 | Hallgren et al. | |
| 8,268,446 B2 | 9/2012 | DeSimone et al. | |
| 8,350,013 B2 | 1/2013 | Sun | |
| 8,440,799 B2 | 5/2013 | Godavarti et al. | |
| 8,455,202 B2 | 6/2013 | Regnier et al. | |
| 8,497,358 B2 | 7/2013 | Suenaga et al. | |
| 8,513,032 B2 | 8/2013 | Jablonski et al. | |

(Continued)

FOREIGN PATENT DOCUMENTS

| | | |
|---|---|---|
| WO | 1991014706 A2 | 10/1991 |
| WO | 1996013524 A1 | 5/1996 |

(Continued)

OTHER PUBLICATIONS

Romig et al.,"Aptamer affinity chromatography: combinatorial chemistry applied to protein purification", Journal of Chromatography B, 731:275-284. (Year: 1999).*
Guthrie et al.,"Assays for cytokines using aptamers", Methods 38: 324-330. (Year: 2006).*
Javaherian et al.,"Selection of aptamers for a protein target in cell lysate and their application to protein purification", Nucleic Acids Research 37(8): e62 pp. 1-10. (Year: 2009).*
Walter et al.,"Aptamers as affinity ligands for downstream processing", Eng. Life Sci. 12(5): 496-506. (Year: 2012).*

(Continued)

*Primary Examiner* — Anand U Desai (74) *Attorney, Agent, or Firm* — Kacvinsky Daisak Bluni PLLC (57) ABSTRACT

In various aspects, the present disclosure pertains to sorbents for isolating at least one target protein from a liquid sample, the sorbents comprising a solid support comprising attached at least one attached high affinity reagent with an affinity for the at least one target protein. Other aspects of the present disclosure include kit that contain such sorbents and methods of treating samples using the same.

19 Claims, 2 Drawing Sheets

(56) References Cited

U.S. PATENT DOCUMENTS

| | | |
|---|---|---|
| 8,524,470 B2 | 9/2013 | Haberger et al. |
| 8,536,316 B2 | 9/2013 | Soice et al. |
| 8,669,120 B2 | 3/2014 | Ylikotila et al. |
| 8,728,828 B2 | 5/2014 | Berg et al. |
| 8,741,600 B2 | 6/2014 | Yamaguchi et al. |
| 8,809,509 B2 | 8/2014 | Takeda et al. |
| 8,895,709 B2 | 11/2014 | Hickman et al. |
| 8,952,138 B2 | 2/2015 | Shultz et al. |
| 9,249,182 B2 | 2/2016 | Herigstad et al. |
| 9,296,791 B2 | 3/2016 | Hober et al. |
| 2002/0030015 A1 | 3/2002 | Stipanovic et al. |
| 2002/0164617 A1 | 11/2002 | Felsch et al. |
| 2003/0087454 A1 | 5/2003 | Schultz et al. |
| 2003/0092012 A1 | 5/2003 | Chenna et al. |
| 2003/0166010 A1 | 9/2003 | Affholter |
| 2003/0170810 A1 | 9/2003 | Vedadi et al. |
| 2004/0029143 A1 | 2/2004 | Van Ness et al. |
| 2004/0033530 A1 | 2/2004 | Awrey et al. |
| 2004/0142488 A1 | 7/2004 | Gjerde et al. |
| 2004/0166504 A1 | 8/2004 | Rossier et al. |
| 2004/0241688 A1 | 12/2004 | Bukusoglu |
| 2005/0107594 A1 | 5/2005 | Sun et al. |
| 2005/0112603 A1 | 5/2005 | Kuo et al. |
| 2005/0124076 A1 | 6/2005 | Tseng et al. |
| 2005/0255473 A1 | 11/2005 | Knezevic et al. |
| 2005/0255554 A1 | 11/2005 | Chilkoti |
| 2005/0258097 A1 | 11/2005 | Gjerde et al. |
| 2006/0000773 A1 | 1/2006 | Glennon et al. |
| 2006/0030696 A1 | 2/2006 | Bonnerjea et al. |
| 2006/0105349 A1 | 5/2006 | Ekenberg et al. |
| 2006/0105391 A1 | 5/2006 | Engel et al. |
| 2006/0234390 A1 | 10/2006 | Slanetz |
| 2006/0257972 A1 | 11/2006 | Ishihara |
| 2007/0009895 A1 | 1/2007 | Yamauchi et al. |
| 2007/0184547 A1 | 8/2007 | Handique et al. |
| 2007/0213513 A1 | 9/2007 | Van Alstine et al. |
| 2008/0132688 A1 | 6/2008 | Zhou |
| 2008/0206894 A1 | 8/2008 | Lyon et al. |
| 2008/0241862 A1 | 10/2008 | Zhao et al. |
| 2008/0312425 A1 | 12/2008 | Bonnerjea et al. |
| 2009/0042216 A1 | 2/2009 | Seraphin et al. |
| 2009/0050566 A1 | 2/2009 | Kozlov et al. |
| 2009/0321358 A1 | 12/2009 | Miyazawa et al. |
| 2010/0129889 A1 | 5/2010 | Sommer-Knudsen |
| 2010/0167283 A1 | 7/2010 | Horgan et al. |
| 2010/0172894 A1 | 7/2010 | Brown et al. |
| 2010/0174052 A1 | 7/2010 | Hjorth et al. |
| 2010/0221844 A1 | 9/2010 | Bian et al. |
| 2010/0227410 A1 | 9/2010 | Takacs et al. |
| 2010/0234577 A1 | 9/2010 | Mazzola et al. |
| 2010/0267581 A1 | 10/2010 | Kiernan et al. |
| 2011/0040075 A1 | 2/2011 | Bonnerjea et al. |
| 2011/0053242 A1 | 3/2011 | Rush et al. |
| 2011/0144311 A1 | 6/2011 | Chmielowski et al. |
| 2012/0009624 A1 | 1/2012 | Sommer-Knudsen et al. |
| 2012/0018381 A1 | 1/2012 | Gjerde et al. |
| 2012/0065380 A1 | 3/2012 | Yoo et al. |
| 2012/0141497 A1 | 6/2012 | Gallo et al. |
| 2012/0177640 A1 | 7/2012 | Burg et al. |
| 2012/0231506 A1 | 9/2012 | Falkenstein et al. |
| 2012/0264920 A1 | 10/2012 | Wang et al. |
| 2012/0283416 A1 | 11/2012 | Frauenschuh et al. |
| 2012/0308555 A1 | 12/2012 | Polakiewicz et al. |
| 2013/0018174 A1 | 1/2013 | Igawa et al. |
| 2013/0045471 A1 | 2/2013 | Gilbert et al. |
| 2013/0096284 A1 | 4/2013 | Ishihara |
| 2013/0197198 A1 | 8/2013 | Sun et al. |
| 2013/0336957 A1 | 12/2013 | Wang et al. |
| 2014/0010820 A1 | 1/2014 | Wang et al. |
| 2014/0018525 A1 | 1/2014 | Goklen et al. |
| 2014/0094593 A1 | 4/2014 | Frauenschuh |
| 2014/0107321 A1 | 4/2014 | Jahagirdar et al. |
| 2014/0134752 A1 | 5/2014 | Bjorkesten et al. |
| 2014/0170727 A1 | 6/2014 | Dryga et al. |
| 2014/0171626 A1 | 6/2014 | Gagnon et al. |
| 2014/0243508 A1 | 8/2014 | Falkenstein et al. |
| 2014/0288278 A1 | 9/2014 | Nti-gyabaah et al. |
| 2014/0323698 A1 | 10/2014 | Duthe et al. |
| 2015/0031581 A1* | 1/2015 | Kema ................. G01N 33/538 506/12 |
| 2015/0065696 A1 | 3/2015 | Wang et al. |
| 2015/0125877 A1 | 5/2015 | Ohlson et al. |
| 2015/0125929 A1 | 5/2015 | Kozlov et al. |
| 2015/0133636 A1 | 5/2015 | Xenopoulos et al. |
| 2015/0152195 A1 | 6/2015 | Iwakura et al. |
| 2015/0239956 A1 | 8/2015 | Koguma et al. |
| 2015/0239991 A1 | 8/2015 | Blein et al. |
| 2015/0361129 A1 | 12/2015 | Natarajan et al. |
| 2016/0002289 A1 | 1/2016 | Kokke et al. |
| 2016/0009762 A1 | 1/2016 | Gagnon et al. |
| 2016/0024147 A1 | 1/2016 | Tustian et al. |
| 2016/0083419 A1 | 3/2016 | Taniguchi et al. |
| 2016/0083452 A1 | 3/2016 | Hickman et al. |
| 2016/0083454 A1 | 3/2016 | Duthe et al. |
| 2016/0090399 A1 | 3/2016 | Kozlov et al. |
| 2016/0102149 A1 | 4/2016 | Burg et al. |
| 2016/0115195 A1 | 4/2016 | Mendiratta et al. |

FOREIGN PATENT DOCUMENTS

| | | |
|---|---|---|
| WO | 1999034220 A2 | 7/1999 |
| WO | 1999041286 A1 | 8/1999 |
| WO | 2000079276 A1 | 12/2000 |
| WO | 2003010512 A2 | 2/2003 |
| WO | 2005049645 A1 | 6/2005 |
| WO | 2005083443 A2 | 9/2005 |
| WO | 2009016431 A1 | 2/2009 |
| WO | 2009058769 A1 | 5/2009 |
| WO | 2009091680 A1 | 7/2009 |
| WO | 2011038894 A1 | 4/2011 |
| WO | 2011087432 A1 | 7/2011 |
| WO | 2011132077 A2 | 10/2011 |
| WO | 2012/015219 A2 | 2/2012 |
| WO | 2012020080 A2 | 2/2012 |
| WO | 2012160536 A1 | 11/2012 |
| WO | 2013041556 A1 | 3/2013 |
| WO | 2015014922 A2 | 2/2015 |
| WO | 2015070068 A1 | 5/2015 |
| WO | 2015070069 A1 | 5/2015 |
| WO | 2015105551 A1 | 7/2015 |
| WO | 2015134785 A1 | 9/2015 |
| WO | 2015135884 A1 | 9/2015 |
| WO | 2015186004 A2 | 12/2015 |
| WO | 2016073401 A1 | 5/2016 |
| WO | 2016/210448 A1 | 12/2016 |

OTHER PUBLICATIONS

International Search Report and Written Opinion for International Patent Application No. PCT/US2019/023340, dated Jun. 19, 2019.

Lonne, M., et al. "Development of an aptamer-based affinity purification method for vascular endothelial growth factor", Biotechnology Reports, 8:16-23, Dec. 1, 2015.

Perret, G., et al., "Aptamer affinity ligands in protein chromatography", Biochimie, 145:98-112, Oct. 18, 2017.

Cho, S., et al. "Microbead-bases affinity chromatography chip using RNA aptamer modified with photocleavable linker", Electrophoresis, 25:3730-3739, Nov. 1, 2004.

Zhang, X., et al., "Highly sensitive thrombin detection by matrix assisted laser desorption ionization-time of flight mass spectrometry with aptamer functionalized coreshell Fe3O4@C@Au magnetic microspheres", Talanta, 88:295-302, Oct. 4, 2011.

Pichon, V., et al. "Aptamer-based-sorbents for sample treatment-are", Analytical and Bioanalytical Chemistry, 407 (3):681-698.

Leriche, G., et al., "Cleavable linkers in chemical biology", Bioorganic & Medicinal Chemistry., 20:571-582, (2012).

Lee, J., "Aptamer Selection for Human Serum Albumin", Honours thesis submitted to the Faculty of Science Department of Chemistry in partial fulfillment of the requirements of the B.Sc. Degree, p. 1-62, Apr. 2011.

\* cited by examiner

NON-ANTIBODY HIGH-AFFINITY-BASED SAMPLE PREPARATION, SORBENT, DEVICES AND METHODS

RELATED APPLICATIONS

This application claims the benefit of U.S. Provisional Application No. 62/646,277, filed Mar. 21, 2018, the entire disclosure of which is incorporated by reference.

FIELD

The present disclosure pertains to high affinity sorbents, devices and methods of using the same, for example, in conjunction with procedures for protein depletion and/or for low-abundance protein enrichment with enhanced recoveries.

BACKGROUND OF THE INVENTION

Identification and quantitation of low-abundance proteins (LAPs) from plasma, serum, or whole blood samples present a challenge to researchers. This is primarily due to presence of high-abundance proteins (HAPs). In this regard, 10-12 HAPs constitute ~95% of the total protein mass of plasma or serum, with human serum albumin being the most prevalent HAP, typically constituting more than half of the total protein mass of plasma or serum. The remainder of the proteins constitute LAPs, and many biomarkers fall into this category. The presence of HAPs increases noise level, which in turn reduces signal-to-noise ratio when preforming analysis.

Two key methods of identifying and quantitating LAPs involve affinity based enrichment of LAPs and/or affinity based depletion of HAPs. Existing products in the marketplace suffer from disadvantages that include (a) the inability to dislodge LAPs bound to carrier proteins such as human serum albumin (which is known to act as a carrier protein for LAPs), (b) the inability to specifically capture the low-abundance proteins and (c) the need for protein precipitation and reconstitution after depleting the HAPs—a step that results in the loss of LAPS.

SUMMARY OF THE INVENTION

In various aspects, the present disclosure is directed to methods of sample treatment that comprise: (a) adding a sample fluid comprising a sample that comprises, or potentially comprises, at least one target protein to a sorbent, the sorbent comprising a solid support with at least one attached high affinity reagent that has a specific high affinity for the target protein, thereby resulting in sorbent with bound target protein; and (b) adding a washing solution that comprises a surfactant and a salt to the sorbent, thereby removing substances for which the at least one high affinity reagent does not have a specific affinity (including said substances indirectly bound to the sorbent by means of attachment to the at least one target protein).

In various embodiments, the target protein is a protein of interest, and the protein of interest is isolated on the sorbent for further processing.

In various embodiments, target protein is not a protein of interest (e.g., where the protein is a high-abundance protein, etc.), and the washing solution may be collected for further downstream processing of the protein of interest.

In various embodiments, which may be used in conjunction with any of the preceding aspects and embodiments, the sample may be selected from a whole blood sample, a plasma sample, and a serum sample.

In various embodiments, which may be used in conjunction with any of the preceding aspects and embodiments, the sample fluid may be prepared by combining the sample with a pretreatment solution that disrupts protein binding. For example, the pretreatment solution may comprise an aqueous acidic or basic solution, for instance, the pretreatment solution may be selected from an aqueous $H_3PO_4$ solution, an aqueous $NH_4OH$ solution, an aqueous ethylenediaminetetraacetic acid (EDTA) solution, an aqueous formic acid solution, an aqueous acetic acid solution, an aqueous trichloroacetic acid (TCA) solution, and an aqueous trifluoroacetic acid (TFA) solution.

In various embodiments, which may be used in conjunction with any of the preceding aspects and embodiments, the washing solution may be a high stringency washing solution.

In various embodiments, which may be used in conjunction with any of the preceding aspects and embodiments, the salt may be a chaotropic salt.

In various embodiments, which may be used in conjunction with any of the preceding aspects and embodiments, the salt may be selected from LiCl, KCl, NaCl, CsCl, LiI, KI, NaI, ScI, LiSCN, KSCN, NaSCN, CsSCN, $Na_2CO_3$, $NaHCO_3$, $NH_4HCO_3$, $Na_2NO_3$, $NaClO_4$, tetramethyl ammonium chloride, tetraethyl ammonium chloride, and trimethylammonium chloride.

In various embodiments, which may be used in conjunction with any of the preceding aspects and embodiments, the surfactant may be an acid labile surfactant. Examples of acid labile surfactants include sodium 3-[(2-methyl-2-undecyl-1,3-dioxolan-4-yl)methoxyl]-1-propanesulfonate, sodium 3-(4-(1,1-bis(hexyloxy)ethyl)pyridinium-1-yl)propane-1-sulfonate, and sodium 3-((1-(furan-2-yl)undecyloxy)carbonylamino)propane-1-sulfonate, among others.

In various embodiments, which may be used in conjunction with any of the preceding aspects and embodiments, the surfactant may be an ionic surfactant. For example, the ionic surfactant may be selected from sodium dodecyl sulfate (SDS), deoxycholate, cholate, and sodium lauroyl sarcosinate, among others.

In various embodiments, which may be used in conjunction with any of the preceding aspects and embodiments, the surfactant may be a nonionic surfactant. For example, the nonionic surfactant may be selected from polysorbate surfactants including polyoxyethylene sorbitan monolaurate (Tween 20) and polyoxyethylene sorbitan monooleate (Tween 80), digitonin, maltosides including n-dodecyl-β-D-maltoside (DDM), n-octyl-β-D-maltoside (DDM), glucosides including octyl-glucoside and decyl-glucoside, 3-[(3-cholamidopropyl) dimethylammonio]-1-propanesulfonate (CHAPS), 3-[(3-cholamidopropyl)dimethylammonio]-1-propanesulfonate hydrate (CHAPSO), and polyethylene glycol p-(1,1,3,3-tetramethylbutyl)-phenyl ether (Triton X-100).

In various embodiments, which may be used in conjunction with any of the preceding aspects and embodiments, the target protein may be a high-abundance protein or the target protein may be a low-abundance protein.

Examples of high-abundance proteins include albumin, immunoglobulin G (IgG), immunoglobulin A (IgA), immunoglobulin M (IgM), immunoglobulin D (IgD), immunoglobulin D (IgE), alpha-1-antitrypsin, transferrin, haptoglobin, fibrinogen, haptoglobulin, α-2-macroglobulin, complement C3, apolipoprotein A-I, apolipoprotein A-II, apolipoprotein B, α-1-acid glycoprotein, ceruloplasmin, complement C4, complement C1q, prealbumin, plasminogen, transthyretin, and combinations thereof, among others.

Examples of low-abundance proteins include cruloplasmin, complement factors C4, C9, C8, and C5, IgD, C1 inhibitor, RBP, iC3b, throxoin binding Globulin, complement proteins, thrombis precursor protein, C-reactive protein, Bb fragment, ferritin, randes, SC5b-9 complex, myoglobin, thryoglobulin, TPA (tissue plasminogen activator), neuron specific enolase, C-peptide, alpha-fetoprotein, TNF-binding proteins, PSA (prostate specific antigen), prostatic acid phosphatase, CEA (carcinoembryonic antigen), myelin basic protein, troponin I, interleukins, MIP_1 alpha, tissue factor, GCSF (granulocyte-colony stimulating factor), interferons, and combinations thereof, among others.

In aspects and embodiments, for example, where the protein is a low-abundance protein, the method may further comprise adding an elution solution to the sorbent, thereby removing the low-abundance protein from the sorbent.

In aspects and embodiments, for example, where the protein is a low-abundance protein, the low-abundance protein may be digested into fragments while bound to the sorbent and the fragments may be eluted. For example, (a) the target protein may be digested by adding a solution comprising a proteolytic enzyme to the sorbent, or (b) the sorbent may comprise an attached proteolytic enzyme and the low-abundance protein may be digested into fragments by activating the proteolytic enzyme (e.g., the low-abundance protein may be digested into fragments by a process that comprises chemically cleaving and releasing the proteolytic enzyme).

In aspects and embodiments, for example, where the protein is a low-abundance protein, the method may further comprise adding an elution solution to the sorbent that causes a complex of the high affinity reagent bound to the low-abundance protein to be released from the sorbent. For example, the high affinity reagent may be linked to the support by an enzymatically cleavable linkage and the elution solution may comprise an enzyme that cleaves the enzymatically cleavable linkage.

In aspects and embodiments, for example, where the protein is a low-abundance protein, (a) the high affinity reagent may be linked to the support by linkage that may be cleaved upon exposure to nucleophilic and/or basic conditions, upon exposure to electrophilic and/or acidic conditions, or upon exposure to reducing conditions, and (b) the sorbent may be exposed to eluting solutions that establish such conditions thus cleaving a complex of the high affinity reagent with bound target protein.

In various aspects, the present disclosure pertains to sorbents for isolating at least one target protein from a liquid sample, the sorbents comprising a solid support comprising attached at least one attached high affinity reagent with an affinity for the at least one target protein.

In various embodiments, at least one high affinity reagent may be selected for their high affinity towards low-abundance proteins, for their high affinity towards high-abundance proteins, or both. Examples of high-abundance proteins include albumin, immunoglobulin G (IgG), immunoglobulin A (IgA), immunoglobulin M (IgM), immunoglobulin D (IgD), immunoglobulin D (IgE), alpha-1-antitrypsin, transferrin, haptoglobin, fibrinogen, haptoglobulin, α-2-macroglobulin, complement C3, apolipoprotein A-I, apolipoprotein A-II, apolipoprotein B, glycoprotein, ceruloplasmin, complement C4, complement C1q, prealbumin, plasminogen, transthyretin, and combinations thereof, among others. Examples of low-abundance proteins include cruloplasmin, complement factors C4, C9, C8, and C5, IgD, C1 inhibitor, RBP, iC3b, throxoin binding Globulin, complement proteins, thrombis precursor protein, C-reactive protein, Bb fragment, ferritin, randes, SC5b-9 complex, myoglobin, thryoglobulin, TPA (tissue plasminogen activator), neuron specific enolase, C-peptide, alpha-fetoprotein, TNF-binding proteins, PSA (prostate specific antigen), prostatic acid phosphatase, CEA (carcinoembryonic antigen), myelin basic protein, troponin I, interleukins, MIP_1 alpha, tissue factor, GCSF (granulocyte-colony stimulating factor), interferons, and combinations thereof, among others.

In various embodiments, which may be used in conjunction with any of the preceding aspects and embodiments, the solid support may comprise an inorganic material, an organic material, or a hybrid organic-inorganic material.

In various embodiments, which may be used in conjunction with any of the preceding aspects and embodiments, the solid support may comprise a polymeric material. For example, the polymeric material may comprise a copolymer comprising a hydrophobic monomer (e.g., divinylbenzene, styrene, etc.) and a hydrophilic monomer (e.g., vinyl pyrrolidone, N-vinyl caprolactam, etc.).

In various embodiments, which may be used in conjunction with any of the preceding aspects and embodiments, the sorbent may be selected from a strong cation exchange sorbent, a strong anion exchange sorbent, a weak cation exchange sorbent, and a weak anion exchange sorbent.

In various embodiments, which may be used in conjunction with any of the preceding aspects and embodiments, the at least one high-affinity reagent may be linked to the solid support by a chemically cleavable linkage. For example, the at least one high-affinity reagent may be linked to the solid support by a linkage that can be cleaved upon exposure to nucleophilic and/or basic conditions, upon exposure to electrophilic and/or acidic conditions, or upon exposure to reducing conditions.

In various embodiments, which may be used in conjunction with any of the preceding aspects and embodiments, the at least one high-affinity reagent may be linked to the solid support by an enzymatically cleavable linkage (e.g., a linkage that is cleavable by a proteolytic enzyme). In certain of these embodiments, the solid support may comprise an attached enzyme (e.g., an enzyme that is linked to the support by a chemically cleavable linkage), which enzyme is adapted to enzymatically cleave the at least one high-affinity reagent from the solid support, thereby allowing a complex of the at least one high-affinity reagent and the target protein to be released from the solid support for further processing.

In various embodiments, which may be used in conjunction with any of the preceding aspects and embodiments, the solid support comprises an attached enzyme that may be adapted to digest the target protein after activation of the attached enzyme.

In various embodiments, which may be used in conjunction with any of the preceding aspects and embodiments, the solid support comprises an attached proteolytic enzyme. For example, the proteolytic enzyme may be selected from trypsin, chymotrypsin, Glu-C, Lys-C, Arg-C, Asp-N, BNPS or NCS/urea, clostripain, CNBr, CNBr (methyl-Cys), CNBr (with acids), formic acid, hydroxylamine, iodosobenzoic acid, Lys-N, neutrophil elastase, NBS, NTCB, pancreatic elastase, pepsin A, prolyl endopeptidase, proteinase K, staphylococcal peptidase I, thermolysin, and combinations thereof, among other possibilities.

In various embodiments, which may be used in conjunction with any of the preceding aspects and embodiments, the solid support comprises an attached proteolytic enzyme that is attached to the solid support through a flexible linker.

In various embodiments, which may be used in conjunction with any of the preceding aspects and embodiments, the solid support comprises an attached proteolytic enzyme that is attached to the solid support through a cleavable linker. For example, the proteolytic enzyme may be attached to the solid support through an enzymatically cleavable linker. As another example, the proteolytic enzyme may be attached to the sorbent through a chemically cleavable linker. For example, the chemically cleavable linker may be selected from chemical linkers that are cleaved upon exposure to nucleophilic and/or basic conditions, chemical linkers that are cleaved upon exposure to electrophilic and/or acidic conditions, chemical linkers that are cleaved upon exposure to reducing conditions, chemical linkers that are cleaved upon exposure to oxidizing conditions, hydroxylamine cleavable linkers, chemical linkers containing bis-succimide esters, chemical linkers containing bis acylazides, and chemical linkers containing bis maleimides.

In various embodiments, which may be used in conjunction with any of the preceding aspects and embodiments, the proteolytic enzyme may be chemically activated by a change in pH or the proteolytic enzyme may be thermally activated by heating or cooling.

In various embodiments, which may be used in conjunction with any of the preceding aspects and embodiments, the sorbent may be disposed in a multi-well strip, a multi-well plate, a column, a single-use cartridge, or an ELISA plate.

In further aspects, the present disclosure pertains to kits that comprises a sorbent in accordance with any of the preceding aspects and embodiments, and one or more kit components selected from (a) a washing solution that comprises a surfactant and a salt, (b) a pretreatment solution, (c) one or more elution solutions, (d) one or more proteolytic enzyme solutions, (e) a collection plate, (f) a cap mat, (g) calibration and reference standards, and (h) instructions for use.

In various embodiments, which may be used in conjunction with any of the preceding aspects and embodiments, the high affinity reagent may be an aptamer or an affimer.

DETAILED DESCRIPTION

The present disclosure pertains to affinity-based methods and to sorbents, devices and kits beneficial in performing affinity-based methods.

In this regard, in some aspects, the present disclosure pertains to sorbents that are useful for isolating at least one target protein from a liquid sample, the sorbents comprising a solid support material having attached thereto affinity reagents such as aptamers or affimers, which have a high affinity for the at least one target protein.

As used herein, an "aptamer" is a nucleic acid (e.g., DNA, RNA, etc.) which selectively binds to a non-nucleic acid target molecule. In some embodiments, the aptamers employed herein may range from 15-80 nucleotide bases in length.

Figure 1:
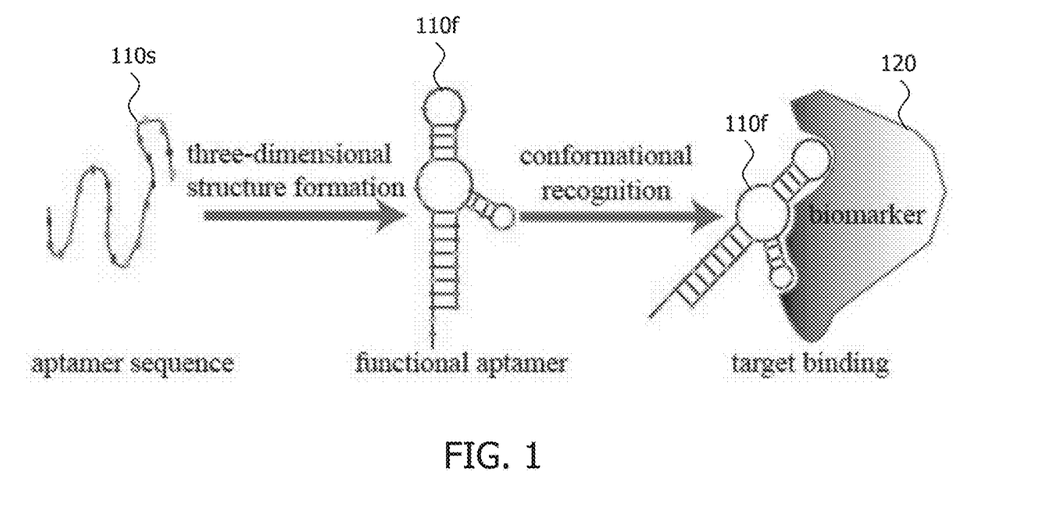
FIG. 1 is a schematic illustration of an aptamer sequence, the aptamer sequence in functional three-dimensional form, as well as the aptamer binding to a target.

FIG. 1 is a schematic illustration of an aptamer sequence 110s, the aptamer sequence in activated functional three-dimensional form 110f, and the aptamer sequence in functional three-dimensional form 110f binding target 120, which is a biomarker in the particular embodiment shown. Aptamers may be activated, for example, by heating (e.g., to 85-90° C.) prior to use.

As a specific example, a human serum albumin aptamer, identified as 23G03 (Oligo #372), is available from Base Pair Technologies, Houston, Tex., USA, which contains 39 bases (without 3'-6T) or 45 bases (with 3'-6T), has a reported molecular weight (including 3'-6T and biotin) of 14,237.4 g/mol and a Kd of 29.1 nM. In addition to biotin, the 3' position may be modified with amine and thiol groups as well. The 5' end may be modified with amine, thiol, fluorescein isothiocyanate (FITC) or cyanine 5 (Cy5). Other aptamers available include, for example, immunoglobulin G (IgG) Fc aptamer, fibrinogen aptamer, and human immunoglobulin M (IgM) mu chain aptamer, among others.

As used herein, an "affimer" is a stable protein molecule which displays peptide loops and which selectively binds to a specific target molecule. Commonly, affimers comprise a fixed core structure with 2 variable loops, which provide for high affinity binding surface for a specific target protein. In certain embodiments, affirmers may be proteins of low molecular weight (e.g., 12-14 kDa), derived from the cysteine protease inhibitor family of cystatins.

Solid support materials useful for the sorbents of the present disclosure include any suitable solid support material to which affinity reagents (e.g., aptamers and/or affimers) may be attached. Examples of solid support materials include organic materials, inorganic materials, and organic-inorganic hybrid materials.

Examples of inorganic materials include, for example, silica-based materials, alumina-based materials, titania-based materials, zirconia-based materials, and carbon-based materials.

In certain beneficial embodiments, the solid support comprises silica based materials formed by hydrolytically condensing one or more organosilane compounds, which may, for example, comprise one or more alkoxysilane compounds. Examples of alkoxysilane compounds include, for instance, tetraalkoxysilanes (e.g., tetramethoxysilane (TMOS), tetraethoxysilane (TEOS), etc.), alkylalkoxysilanes such as alkyltrialkoxysilanes (e.g., methyl trimethoxysilane, methyl triethoxysilane (MTOS), ethyl triethoxysilane, etc.) and bis(trialkoxysilyl)alkanes (e.g., bis(trimethoxysilyl)methane, bis(trimethoxysilyl)ethane, bis(triethoxysilyl)methane, bis(triethoxysilyl)ethane (BTE), etc.), as well as combinations of the foregoing.

In certain embodiments, the silica-based materials may be prepared from two monomers: a tetraalkoxysilane such as TMOS or TEOS and an alkylalkoxysilane such as MTOS or bis(trialkoxysilyl)alkanes such as BTEE. When BTEE is employed as a monomer, the resulting materials are sometimes referred to as ethylene bridged hybrid (BEH) materials and offer various advantages over conventional silica-based materials, including the ability to control surface silanol activity, chemical and mechanical stability.

In certain beneficial embodiments, the solid support comprises an organic or organic-inorganic hybrid material in the form of a polymer. In particular embodiments, the polymer may be a copolymer comprising a hydrophilic monomer (e.g., e.g., N-vinyl pyrrolidone, N-vinyl caprolactam, etc.) and a hydrophobic monomer (e.g., divinylbenzene, styrene, etc.).

In certain embodiments, the sorbent may be an ion exchange sorbent, for example, a strong cation exchange sorbent (e.g., containing a polymer that comprises a monomer having one or more strong anionic groups such as sulfonate groups, for instance, divinylbenzene having one or more sulfonate groups), a strong anion exchange sorbent (e.g., containing a polymer that comprises a monomer having one or more strong cationic groups such as quaternary ammonium groups, for instance, divinylbenzene having one or more quaternary ammonium groups), a weak cation exchange sorbent (e.g., containing a polymer that comprises a monomer having one or more weak anionic groups such as carboxyl groups, for instance, divinylbenzene having one or more carboxyl groups), or a weak anion exchange sorbent (e.g., containing a polymer that comprises a monomer having one or more weak cationic groups such as primary, secondary or tertiary amine groups, for example, divinylbenzene having one or more primary, secondary or tertiary amine groups, for instance, one or more piperazine groups.

In various aspects, the sorbents employed are particulate sorbents that comprise particles of solid support materials such as those described above having affinity reagents attached thereto.

In other aspects, the sorbet may be a monolith, an aerogel, a membrane, a hydrogel, fibrous materials or a microchannel on a chip having affinity reagents attached thereto.

Sorbent particles for use in conjunction with the present disclosure may vary widely in size and may range, for example, from about 1 um to about 100 μm in diameter, among other particle sizes.

Sorbent particles for use in conjunction with the present disclosure may be non-porous, superficially porous or fully porous, including particles with pores having a diameter ranging from about 8 nm to about 2500 nm, among other values.

Sorbent particles for the use in conjunction with the present disclosure may be porous or non-porous magnetic particles.

Affinity reagents (e.g., aptamers and/or affimers) may be attached to the solid support material using any suitable bonding scheme, including covalent and non-covalent attachment.

Figure 2A:
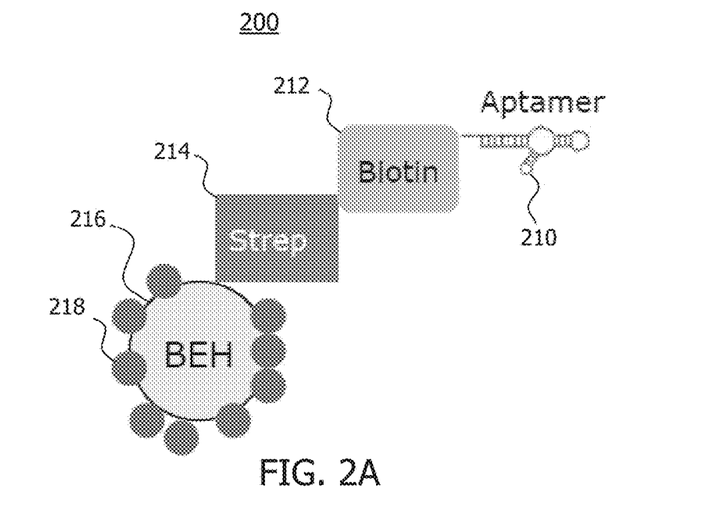
FIG. 2A is a schematic illustration of a high affinity reagent that targets at least a single protein in the sample, attached to a solid sorbent particle in accordance with an embodiment of the present disclosure.

For example, with reference to FIG. 2A, there is shown schematic illustration of a sorbent particle with attached high affinity reagent 200 in accordance with an embodiment of the present disclosure that is capable of targeting at least a single protein in a sample. In the embodiment shown, an aptamer 210 with an attached biotin molecule 212 (i.e., a biotinylated aptamer) is attached to a sorbent particle (e.g., a BEH particle 216), with an attached streptavidin molecule 214, like that described in the Examples below). Numeral 218 designates casein.

Devices in accordance with the present disclosure commonly include high affinity sorbents as described herein in a packed sorbent bed.

Devices in accordance with the present disclosure commonly include a housing having a chamber for accepting and holding high affinity sorbents. In various embodiments, the housing may be provided an inlet and an outlet.

The construction materials for the housing include inorganic materials, for instance, metals such as stainless steel and ceramics such as glass, as well as synthetic polymeric materials such as polyethylene, polypropylene and polyether ether ketone (PEEK), and polycarbonate.

In certain embodiments, the device may include one or more filters which act to hold the sorbent in a housing. Exemplary filters may be, for example, in a form of membrane, screen, frit or spherical porous filter.

In certain embodiments, a solution received in the housing may flow into the high affinity sorbent spontaneously, for example, capillary action. Alternatively, the flow may be generated through the sorbent by external forces, such as gravity or centrifugation, or by applying a vacuum to an outlet of the housing or positive pressure to an inlet of the housing.

Specific examples of housings for use in the present disclosure include, for example, a syringe, an injection cartridge, a column (e.g., a microbore column, capillary column or nanocolumn), a multi-well device such as a 4 to 8-well rack, a 4 to 8-well strip, a 48 to 96-well plate, a 96 to 384-well micro-elution plate, micro-elution tip devices, including a 4 to 8-tip micro-elution strip, a 96 to 384-micro-elution tip array, a single micro-elution pipet tip, a thin layer plate, a microliter plate, a spin tube or a spin container.

Multi-well formats are commonly used with robotic fluid dispensing systems. Typical multi-well formats include 48-, 96-, and 384-well standard plate formats, although other formats are clearly possible.

In various aspects, the present disclosure pertains to methods of performing sample enrichment which comprise contacting a sample fluid, comprising a sample that comprises at least one target protein with a sorbent in accordance with the present disclosure.

The sample fluid can be any fluid containing, or potentially containing, a target protein of interest. In some embodiments, the sample fluid may be in the form, for example, of an aqueous solution or a water-miscible organic solution.

In some embodiments, the sample fluid is or is derived from a biological sample. Exemplary biological samples include biological fluids, biological tissues, biological matrices, embedded tissue samples, inclusion bodies, cells (e.g., one or more types of cells), and cell culture supernatants. Particular examples of biological samples may include whole blood, blood plasma, blood serum, urine, cerebrospinal fluid, synovial fluid sputum, semen, saliva, tears, gastric juices and other biological fluids, including extracts of tissues, such as liver tissue, muscle tissue, brain tissue, heart tissue and the like.

In some embodiments, the sample fluid is or is derived from a reaction mixture, preparative HPLC, a chromatographic eluent or fraction, or an environmental sample.

In some embodiments, the sample fluid may be prepared by process that comprises addition of a pretreatment solution that disrupts protein binding. For example, in some instances, the sample fluid may comprise a biological sample combined with a pretreatment solution that disrupts protein binding. Examples of pretreatment solutions that disrupt protein binding include aqueous acidic solutions and aqueous basic solutions. In certain particular embodiments, aqueous pretreatment solutions may be employed which comprise with ethylenediaminetetraacetic acid (EDTA), formic acid, acetic acid, trichloroacetic acid (TCA), trifluoroacetic acid (TFA), phosphoric acid, $NH_4OH$, and combinations thereof, among others.

In some embodiments, the target protein may comprise, for example, one or more high-abundance proteins.

Examples of high-abundance proteins include albumin, a high-abundance immunoglobulin such as immunoglobulin G (IgG), immunoglobulin A (IgA), immunoglobulin M (IgM), immunoglobulin D (IgD) and immunoglobulin E (IgE), alpha-1-antitrypsin, transferrin, haptoglobin, fibrinogen, haptoglobulin, α-2-macroglobulin, complement C3, apolipoprotein A-I, apolipoprotein A-II, apolipoprotein B, α-1-acid glycoprotein, ceruloplasmin, complement C4, complement C1q, prealbumin, plasminogen, transthyretin and combinations thereof.

In some embodiments, the target protein may comprise, for example, one or more low-abundance proteins.

Examples of low-abundance proteins include cruloplasmin, complement factors such as C4, C9, C8, C5, IgD, C1 inhibitor, RBP, iC3b, throxoin binding Globulin, complement proteins, thrombis precursor protein, C-reactive protein, Bb fragment, ferritin, randes, SC5b-9 complex, myoglobin, thryoglobulin, TPA (tissue plasminogen activator), neuron specific enolase, C-peptide, alpha-fetoprotein, TNF-binding proteins, PSA (prostate specific antigen), prostatic acid phosphatase, CEA (carcinoembryonic antigen), myelin basic protein, troponin I, interleukins, MIP_1 alpha, tissue factor, GCSF (granulocyte-colony stimulating factor), interferons, and combinations thereof.

In certain embodiments pertaining to LAPs, the affinity reagents may be attached to the solid support material by a cleavable linker such that the affinity reagents, along with any bound protein, may be released from the support. Cleavable linkers including chemically labile linkers and enzymatically cleavable linkers.

Enzymatically cleavable linkers include peptide-based linkers having specific sequences that are cleaved upon exposure to suitable enzymes (e.g., a protease), particularly enzymes that are specific to particular peptide sequences, for example, Caspase-1, Caspase-2, Caspase-3, Caspase-4, Caspase-5, Caspase-6, Caspase-7, Caspase-8, Caspase-9, Caspase-10, cathepsin B, Enterokinase, Factor Xa, Granzyme B, HRV3C protease, matrix metalloproteinase-2, TEV protease, Thrombin, and so forth.

Chemically labile linkers include linkers that are cleaved upon exposure to nucleophilic and/or basic conditions (e.g., based on cleavable groups such as dialkyl dialkoxysilane, cyanoethyl, sulfone, ethylene glycolyl disuccinate 2-N-acyl nitrobenzenesulronamide, α-thiophenylester, unsaturated vinyl sulfide, sulfonamide after activation, malondialdehyde (MDA)-indole derivative, levulinoyl ester, hydrazine, acylhydrazone, and alkyl thioester, among other cleavable groups). Chemically labile linkers also include linkers that are cleaved upon exposure to electrophilic and/or acidic conditions (e.g., linkers based on cleavable groups such as paramethoxybenzyl derivatives, tert-butylcarbamate analogues, dialkyl or diaryl dialkoxysilanes, orthoesters, acetal, aconityl, hydrazone, β-thioproprionate, phosphoramidate, imine, trityl, vinyl ether, polyketal, alkyl 2-(diphenylphosphino)benzoate derivatives, and 4-(4'-acetylphenoxy) butanoic acid, among other cleavable groups). Chemically labile linkers further include linkers that are cleaved upon exposure to reducing conditions (e.g., linkers such as disulfide bridges, diazo linkers, etc.), linkers that can be cleaved upon exposure to oxidizing conditions such as those containing glycols and hydroxylamine cleavable linker such as those containing esters. Chemical liable homofuctional linkers such as those containing cleavable bis-succimide esters, bis acylazides, and bis maleimides.

In various embodiments, the methods described herein may first comprise contacting a sample fluid that comprises one or more target proteins with a sorbent that comprises a solid support with attached affinity reagents (e.g., aptamers or affimers) that have a specific affinity for the one or more target proteins (such sorbents are described in more detail above), thereby resulting in sorbent bound to the one or more target proteins. In this regard, different affinity reagents can be attached to the sorbent to allow capture of multiple target proteins simultaneously. The sorbent may beneficially comprise a molar excess of attached affinity reagents relative to the one or more target proteins in the sample fluid.

Figure 2B:
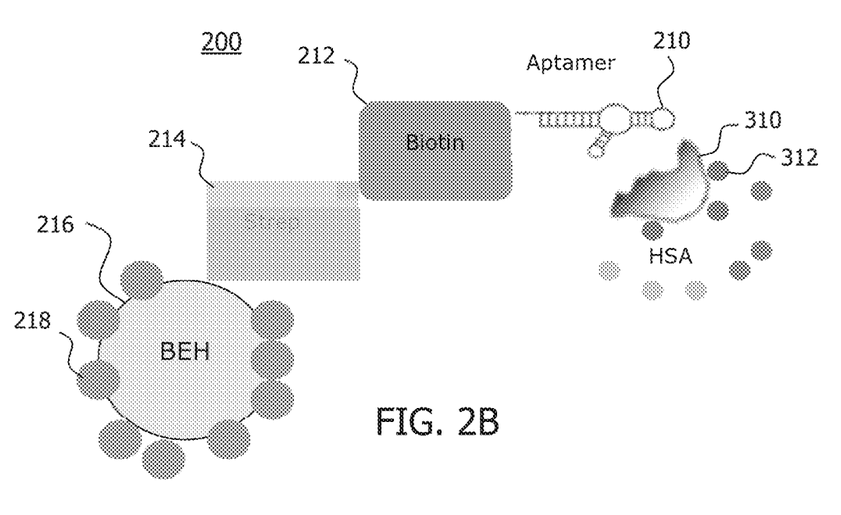
FIG. 2B Is the schematic illustration of a high affinity reagent attached to a sorbent particle pulling down its target protein and non-target proteins which are attached to target proteins by weak chemical interactions.

This process is frequently referred to as a "loading" process, and commonly involves passing the sample fluid through a device that contains the sorbent (such devices are described in more detail above). During loading, the one or more target proteins, along with various unintended non-target substances including non-target proteins, are adsorbed onto the sorbent. For example, a sorbent particle with attached high affinity reagent 200 like that shown in FIG. 2A can be used to bind to a target protein 310 as well as various non-target proteins 312 which are attached to target protein 310 by weak chemical interactions, as shown schematically in FIG. 2B.

Contact time and/or flow rate during loading may be optimized for proper diffusion kinetics and binding of the one or more target proteins to the sorbent. If desired the sample fluid may be passed multiple times through the device.

In certain embodiments, for example, where the sorbent is not readily water-wettable, conditioning and equilibrating steps may be performed prior to sample loading. For example, in an exemplary embodiment, the conditioning may be performed with methanol, ethanol, propanol, isopropyl alcohol, water and a mixture thereof, among other possibilities. For example, an exemplary embodiment, the equilibrating solution may have similar or same ionic strength with the sample solution to provide equilibrated partitioning environments in the sorbents when the sample solution is loaded. Exemplary equilibrating solution/solvent may be, but not limited to, water, an aqueous solution such as a buffer solution (e.g., a phosphate buffer solution), a water-miscible organic solvent solution and the like.

In certain embodiments, for example, where the sorbent is sufficiently water-wettable, conditioning and equilibrating may be omitted before sample loading.

Once a sample is loaded onto the sorbent, one or more washing solutions may then be contacted with the sorbent to separate non-target substances (e.g., substances for which the affinity reagents do not have a specific affinity) from the target protein(s) that are bound to the sorbent, thereby resulting in the elution of non-target substances, while allowing the target protein(s) to remain retained on the sorbent.

In various embodiments, the one or more washing solutions may comprise a low stringency washing solution, a high stringency washing solution, or both.

As used herein, a "high stringency" washing solution is one that enables disruption of high affinity interactions between a target protein (P) and a ligand (L), specifically, interactions between a target protein (P) and a ligand (L) of $10^{-8}$ M Kd or more, where Kd is the equilibrium dissociation constant. Where the formation of a ligand-protein complex, LP can be described by a two-state process L+P⇌LP, the corresponding equilibrium dissociation constant is, $$K_d = \frac{[L][P]}{[LP]},$$

where [L], [P] and [LP] represent molar concentrations of the protein (P), ligand (L) and ligand-protein complex (LP), respectively. As used herein, a "low stringency" washing solution is one that enables disruption of low affinity interactions, specifically, interactions between a target protein (P) and a ligand (L) of or $10^{-8}$M Kd or more.

In the present disclosure, a high affinity reagent that has a specific high affinity for a target protein is generally one in which interactions between the target protein (P) and the ligand (L) (which in this case is the high affinity reagent) is $10^{-8}$M Kd or more.

In various embodiments, the one or more washing solutions may comprise one or more surfactants and one or more chaotropic salts.

Examples of chaotropic salt may include the following, among others: LiCl, KCl, NaCl, CsCl, LiI, KI, NaI, ScI, LiSCN, KSCN, NaSCN, CsSCN, $Na_2CO_3$, $NaHCO_3$, $NH_4HCO_3$, $Na_2NO_3$, $NaClO_4$, tetramethyl ammonium chloride, tetraethyl ammonium chloride, and trimethylammonium chloride, among others.

In various embodiments, the one or more surfactants may comprise an ionic surfactant or a non-ionic surfactant. Examples of ionic surfactants may include the following, among others: sodium dodecyl sulfate (SDS), deoxycholate, cholate, and sodium lauroyl sarcosinate (sarkosyl). Examples of nonionic surfactants may include the following, among others: polysorbate surfactants including polyoxyethylene sorbitan monolaurate (Tween 20) and polyoxyethylene sorbitan monooleate (Tween 80), digitonin, maltosides including n-dodecyl-β-D-maltoside (DDM), n-octyl-β-D-maltoside (DDM), glucosides including octyl-glucoside and decyl-glucoside, 3-[(3-cholamidopropyl)dimethylammonio]-1-propanesulfonate (CHAPS), 3-[3-cholamidopropyl)dimethylammonio]-1-propanesulfonate hydrate (CHAPSO), and polyethylene glycol p-(1,1,3,3-tetramethylbutyl)-phenyl ether (Triton X-100).

In various embodiments, the one or more surfactants may comprise one or more acid labile surfactants. Examples of acid labile surfactants may include the following, among others: sodium 3-[(2-methyl-2-undecyl-1,3-dioxolan-4-yl)methoxyl]-1-propanesulfonate (available from Waters Corporation, Milford, Mass., USA, as RapiGest™ SF Surfactant), sodium 3-(4-(1,1-bis(hexyloxy)ethyl)pyridinium-1-yl) propane-1-sulfonate (available as PPS Silent™ Surfactant from Expedeon Ltd., Over Cambridgeshire, United Kingdom), and sodium 3-((1-(furan-2-yl)undecyloxy)carbonylamino)propane-1-sulfonate (available as ProteaseMAX™ from Promega Corporation, Fitchburg, Wis., USA).

HAPs. In some embodiments, the target protein may be one or more HAPs and the methods described herein may be used to deplete the one or more HAPs from the sample fluid, thereby improving the ability to subsequently identify, quantify or otherwise process various non-target substances, including one or more LAPs, in the sample fluid. In some embodiments, LAPs from the sample can be or captured and enriched using a second device containing high affinity sorbent specific for capturing the LAPs.

The one or more washing solutions may comprise a low stringency wash, a high stringency wash, or both.

For example, a low stringency wash may be performed using a solution that contains low power surfactant and moderate salt concentration to disrupt low Kd protein-protein interactions between one or more target proteins (e.g., HAPs) other plasma proteins (e.g., LAPs). Alternately or in addition, a high stringency wash may be performed with a solution that contains a powerful surfactant such as SDS and chaotropic salt to disrupt essentially any interactions other than the high affinity interactions between the sorbent and the one or more target proteins. The powerful surfactant may act to maintain the protein in a semi-denatured to fully denatured state, if that is beneficial for affinity capture of the one or more target proteins.

In these embodiments, the sorbent with the attached one or more target proteins (e.g., HAPs) may be discarded or regenerated after use by washing with 1M NaOH among other possibilities (depending on the type of aptamer-target molecule complex) followed with equilibration of the sorbent in the solvent used in the loading process.

In these embodiments, after one or more washing solutions have been contacted with the sorbent to separate non-target substances from the one or more target proteins bound to the sorbent, the one or more washing solutions are collected for further processing, which may include, for example, identifying, quantifying or otherwise processing various LAPs in the one or more washing solutions. Prior to doing so, it may be desirable to remove the one or more surfactants and one or more chaotropic salts from the one or more washing solutions. This may be conducted, for example, using suitable solid-phase extraction methods, such as those employing Oasis® HLB sorbent, Oasis® PRIME HLB, Oasis® MCX, or Oasis® MAX (Waters Corp.), among others.

Notably, identification and quantitation of LAPs from biological samples such as plasma, serum, or whole blood samples present a challenge to researchers, primarily due to the presence of HAPs, with one HAP (albumin) constituting over half of the total protein mass of plasma/serum, and a handful of HAPs (albumin, IgG, transferrin, fibrinogen, IgA, haptoglobin, α-1-antitrypsin, α-2-macroglobulin, IgM, apolipoprotein A-I, α-1-acid glycoprotein, complement C3, apolipoprotein A-II, transthyretin) constituting ~95% of the total protein mass of plasma/serum. Depleting one or more these HAPs will improve the ability of researchers to identify, quantify or otherwise process LAPS. By utilizing high affinity sorbents in which high affinity reagents such as aptamers or affimers are bound to a solid support, one or more washing solutions may be employed to dislodge non-target substances (e.g., LAPs) from the HAP's bound to sorbent, which include washing solutions which would otherwise have a stringency that is so great that the HAPs would be removed from the sorbent along with the non-target substances. In this way, HAPs may be removed from LAPs without need for precipitation and reconstitution steps, which are commonly employed in the art and which result in LAP loss. Thus, in various embodiments, methods described herein are used to prepare samples (e.g., samples obtained after removal of HAPs during a depletion procedure) for further analysis and/or processing.

LAPs. In some embodiments, the target protein may be one or more proteins (e.g., one or more LAPs) that have been identified for enrichment. In these embodiments, the methods described herein may be used to enrich those proteins from the sample fluid.

In this regard, the one or more washing solutions may comprise a high stringency wash. By utilizing high affinity sorbents in which high affinity reagents such as aptamers or affimers are bound to a solid support, one or more high stringency washing solutions may be employed to dislodge non-target substances, including HAPs, from the sorbent which might otherwise cause the one or more proteins being enriched (e.g., one or more LAPs) to be inadvertently removed from the sorbent along with the non-target substances.

For example, a high stringency wash may be performed with a solution that contains a powerful surfactant such as SDS, among others, to disrupt essentially any interactions other than the high affinity interactions (e.g., those less than $10^{-8}$ M Kd) between the sorbent bound affinity reagent and the one or more target proteins. The powerful surfactant may also act to maintain the protein in a semi-denatured to fully denatured state, if that is beneficial for affinity capture of the one or more target proteins.

In these embodiments where the target protein(s) may be one or more proteins (e.g., one or more LAPS) that have been identified for enrichment, after one or more washing solutions have been contacted with the sorbent to separate non-target substances from the one or more target proteins that are bound to the sorbent, the one or more target proteins on the sorbent may be subjected to further processing. The one or more washing solutions, on the other hand, may be discarded.

Further processing of the target protein(s) bound to the sorbent in such embodiments may include, for example, quantifying or otherwise processing various LAPs attached to the sorbent.

For instance, in some embodiments, the one or more target proteins may be subjected to digestion while remaining on the sorbent. For example, the bound target protein may be digested by one or more proteolytic enzymes, for example, one or more endoproteinases such as trypsin, chymotrypsin, Glu-C or Lys-C, which hydrolytically break peptide bonds in the target proteins, thereby fragmenting the target proteins into peptides. Additional proteolytic species/conditions that may be employed to break peptide bonds include Arg-C, Asp-N, BNPS or NCS/urea, clostripain, CNBr, CNBr (methyl-Cys), CNBr (with acids), formic acid, Glu-C, hydroxylamine, iodosobenzoic acid, Lys-N, mild acid hydrolysis, neutrophil elastase, NBS, NTCB, pancreatic elastase, pepsin A, prolyl endopeptidase, proteinase K, staphylococcal peptidase I, and thermolysin, among others.

The proteolytic enzyme may be, for example, added to the sorbent bed. Alternatively, a proteolytic enzyme may be chemically linked to the sorbent, in which case a linker may be employed to assist the enzyme with contacting and digesting the bound target protein. The enzyme could also be bound on the support using cleavable linker, where the cleavage is triggered chemically, thereby allowing the release of the enzyme to do the digestion. The proteolytic enzyme attached to the sorbent may be activated, for example, by temperature elevation or by establishing a particular pH. If using the added enzyme or cleaved enzyme, a sample preparation step may be employed to remove the enzyme as well as autolysis products in some cases, before the analysis of the target protein. After the digestion of the attached LAP the affinity sorbent may be regenerated or discarded.

In some embodiments, prior to digestion, the one or more bound target proteins may be subjected to a reduction and alkylation. For instance, the one or more bound target proteins may be subjected to disulfide reduction using a suitable reducing agent such as tris(2-carboxyethyl) phosphine (TCEP) or dithiothreitol (DTT), and the free sulfhydryl groups on the cysteine residues may be alkylated with alkylating reagents such as iodoacetamide or iodoacetic acid to irreversibly prevent the free sulfhydryls from reforming disulfide bonds.

After digestion, the resulting peptide mixture may be optionally mixed with a buffer (e.g., a buffer having neutralizing properties). The peptide mixture may then be used downstream for protein quantification.

In some embodiments, for instance, where the affinity reagent is attached to the sorbent via a cleavable linkage, then the affinity reagent with attached target protein(s) may be released from the support for further processing.

For example, the affinity reagent may be attached to the sorbent, via a linkage that is cleaved upon exposure to nucleophilic and/or basic conditions, upon exposure to electrophilic and/or acidic conditions, or upon exposure to reducing conditions as discussed above, in which case the sorbent may be exposed eluting solutions that establish such conditions. The affinity reagent may be attached to the sorbent via a linkage that enzymatically cleavable, for example, the linkage may include peptide-based linkers having specific sequences that are cleaved upon exposure to suitable enzymes (e.g., a protease), particularly enzymes that are specific to particular peptide sequences such as those previously discussed. Such enzymes could be added to the sorbent or, alternatively, such enzymes may be chemically linked to the sorbent, in which case a linker may be employed to assist the enzymes with contacting the cleavable linkage by which the affinity reagent is bound to the sorbent. In some instances, the enzyme may be attached to the particle through a cleavable linker, in which case the linker may be cleaved to release the enzyme that is then used to cleave the affinity reagent. Enzymes attached to the sorbent may be activated, for example, by temperature elevation or by establishing a particular pH or solvent system.

As indicated above, in various embodiments, methods described herein may further comprise analyzing samples (e.g., samples obtained after removal of HAPs during a depletion procedure, samples obtained after removal or digestion of LAPs captured by sorbent in an enrichment procedure, etc.) using analytical instruments and/or techniques, for example, liquid chromatography (LC), including high performance liquid chromatography (HPLC) and ultra-high performance liquid chromatography (UHPLC), mass spectrometry (MS), including tandem mass spectrometry (MS/MS) electrospray ionization mass spectrometry (ESI-MS), matrix-assisted laser desorption/ionization mass spectrometry (MALDI-MS), time-of-flight mass spectrometry (TOFMS), nuclear magnetic resonance, infrared analysis, ultraviolet analysis, or a combination thereof. For instance, in some embodiments, the processed samples may be analyzed using liquid chromatography, such as HPLC or UHPLC, in combination with mass spectrometry, such as MALDI-MS or ESI-MS, examples of which include liquid chromatography-mass spectrometry (LC-MS) techniques and liquid chromatography-mass spectrometry/mass spectrometry (LC-MS/MS) techniques. In certain cases, analytical samples may be evaporated to dryness, and then reconstituted in another solution before being injected into a liquid chromatography system.

Kits may also be provided which comprises a high affinity sorbent as described elsewhere herein and one or more of any of the following: (a) a washing solution that comprises a surfactant and a salt as described elsewhere herein, (b) a pretreatment solution as described elsewhere herein, (c) one or more elution solutions as described elsewhere herein, (d) a collection plate or collection barrel, (e) a cap mat, (f) calibration and reference standards, and (g) instructions for use. The sorbent may be disposed in a housing, for example, in a column, a single-use cartridge, a multi-well strip, a multi-well plate, or other housing as described elsewhere herein.

Further aspects of the present disclosure are set forth in the following enumerated paragraphs:

Aspect A1. A method of sample treatment comprising: adding a sample fluid comprising a sample that comprises, or potentially comprises, at least one target protein to a sorbent, the sorbent comprising a solid support with at least one attached high affinity reagent that has a specific high affinity for the target protein, thereby resulting in sorbent with bound target protein; and adding a washing solution that comprises a surfactant and a salt to the sorbent, thereby removing substances for which the at least one high affinity reagent does not have a specific affinity including said substances that are indirectly bound to the sorbent by means of attachment to the target protein.

Aspect A2. The method of aspect A1, wherein (a) when the target protein is a protein of interest, the protein of interest is isolated on the sorbent for further processing or (b) when the target protein is not a protein of interest, the washing solution is collected for further downstream processing of the protein of interest.

Aspect A3. The method of any of aspects A1-2, wherein the sample is selected from a whole blood sample, a plasma sample, and a serum sample.

Aspect A4. The method of any of aspects A1-A3, wherein the sample fluid is prepared by combining the sample with a pretreatment solution that disrupts protein binding.

Aspect A5. The method of aspect A4, wherein the pretreatment solution comprises an aqueous acidic or basic solution.

Aspect A6. The method of aspect A4, wherein the pretreatment solution is selected from an aqueous $H_3PO_4$ solution, an aqueous $NH_4OH$ solution, an aqueous ethylenediaminetetraacetic acid (EDTA) solution, an aqueous formic acid solution, an aqueous acetic acid solution, an aqueous trichloroacetic acid (TCA) solution, and an aqueous trifluoroacetic acid (TFA) solution.

Aspect A7. The method of any of aspects A1-A6, wherein the washing solution is a high stringency washing solution.

Aspect A8. The method of any of aspects A1-A7, wherein the salt is a chaotropic salt.

Aspect A9. The method of any of aspects A1-A7, wherein the salt is selected from LiCl, KCl, NaCl, CsCl, LiI, KI, NaI, ScI, LiSCN, KSCN, NaSCN, CsSCN, $Na_2CO_3$, $NaHCO_3$, $NH_4NCO_3$, $Na_2NO_3$, $NaClO_4$, tetramethyl ammonium chloride, tetraethyl ammonium chloride, and trimethylammonium chloride.

Aspect A10. The method of any of aspects A1-A9, wherein the surfactant is an acid labile surfactant.

Aspect A11. The method of aspect A10, wherein the acid labile surfactant is selected from sodium 3-[(2-methyl-2-undecyl-1,3-dioxolan-4-yl)methoxyl]-1-propanesulfonate, sodium 3-(4-(1,1-bis(hexyloxy)ethyl)pyridinium-1-yl)propane-1-sulfonate, and sodium 3-((1-(furan-2-yl)undecyloxy)carbonylamino)propane-1-sulfonate.

Aspect A12. The method of any of aspects A1-A9, wherein the surfactant is an ionic surfactant.

Aspect A13. The method of aspect A12, wherein the ionic surfactant is selected from sodium dodecyl sulfate (SDS), deoxycholate, cholate, and sodium lauroyl sarcosinate.

Aspect A14. The method of any of aspects A1-A9, wherein the surfactant is a nonionic surfactant.

Aspect A15. The method of aspect A14, wherein the nonionic surfactant is selected from polysorbate surfactants including polyoxyethylene sorbitan monolaurate (Tween 20) and polyoxyethylene sorbitan monooleate (Tween 80), digitonin, maltosides including n-dodecyl-β-D-maltoside (DDM), n-octyl-β-D-maltoside (DDM), glucosides including octyl-glucoside and decy-glucoside, 3-[3-cholamidopropyl) dimethylammonio]-1-propanesulfonate (CHAPS), 3-[(3-cholamidopropyl)dimethylammonio]-1-propane-sulfonate hydrate (CHAPSO), and polyethylene glycol p-(1,1,3,3-tetramethylbutyl)-phenyl ether (Triton X-100).

Aspect A16. The method of any of aspects A1-A15, wherein the target protein is a high-abundance protein.

Aspect A17. The method of aspect A16, wherein the high-abundance protein is selected from albumin, immunoglobulin G (IgG), immunoglobulin A (IgA), immunoglobulin M (IgM), immunoglobulin D (IgD), immunoglobulin D (IgE), alpha-1-antitrypsin, transferrin, haptoglobin, fibrinogen, haptoglobulin, α-2-macroglobulin, complement C3, apolipoprotein A-I, apolipoprotein A-II, apolipoprotein B, α-1-acid glycoprotein, ceruloplasmin, complement C4, complement C1q, prealbumin, plasminogen, transthyretin, and combinations thereof.

Aspect A18. The method of any of aspects A1-A15, wherein the target protein is a low-abundance protein.

Aspect A19. The method of aspect A18, wherein the low-abundance protein is selected from cruloplasmin, complement factors C4, C9, C8, and C5, IgD, C1 inhibitor, RBP, iC3b, throxoin binding Globulin, complement proteins, thrombis precursor protein, C-reactive protein, Bb fragment, ferritin, randes, SC5b-9 complex, myoglobin, thryoglobulin, TPA (tissue plasminogen activator), neuron specific enolase, C-peptide, alpha-fetoprotein, TNF-binding proteins, PSA (prostate specific antigen), prostatic acid phosphatase, CEA (carcinoembryonic antigen), myelin basic protein, troponin I, interleukins, MIP_1 alpha, tissue factor, GCSF (granulocyte-colony stimulating factor), interferons, and combinations thereof.

Aspect A20. The method of any of aspects A18-A19, further comprising adding an elution solution to the sorbent, thereby removing the low-abundance protein from the sorbent.

Aspect A21. The method of any of aspects A18-A19, wherein the low-abundance protein is digested into fragments while bound to the sorbent and the fragments are eluted.

Aspect A22. The method of aspect A21, wherein the target protein is digested by adding a solution comprising a proteolytic enzyme to the sorbent.

Aspect A23. The method of aspect A21, wherein the sorbent comprises an attached proteolytic enzyme and wherein the low-abundance protein is digested into fragments by activating the proteolytic enzyme.

Aspect A24. The method of aspect A21, where the sorbent comprises an attached cleavable enzyme and wherein the low-abundance proteins is digested into fragments by a process that comprises chemically cleaving and releasing the proteolytic enzyme.

Aspect A25. The method of any of aspects A18-A19, wherein the high affinity reagent is linked to the support by an enzymatically cleavable linkage and wherein the elution solution comprises an enzyme that cleaves the enzymatically cleavable linkage.

Aspect A26. The method of aspect A18-A19, wherein the high affinity reagent is linked to the support by linkage that is cleaved upon exposure to nucleophilic and/or basic conditions, upon exposure to electrophilic and/or acidic conditions, or upon exposure to reducing conditions, wherein the sorbent may be exposed to eluting solutions that establish such conditions thus cleaving a complex of the high affinity reagent with bound target protein.

Aspect A27. The method of any of aspects A1-A26, wherein the high affinity reagent is an aptamer or an affimer.

Aspect B1. A sorbent for isolating at least one target protein from a liquid sample, the sorbent comprising a solid support comprising attached aptamers or affimers with an affinity for the at least one target protein.

Aspect B2. The sorbent aspect B1, wherein the solid support comprises silica.

Aspect B3. The sorbent on aspect B1 where in the solid support comprises a hybrid material Aspect B4. The sorbent of any of aspects B1-B3, wherein the solid support comprises a polymeric material.

Aspect B5. The sorbent of aspect B4, wherein the polymeric material comprises a copolymer comprising a hydrophobic monomer and a hydrophilic monomer.

Aspect B6. The sorbent of aspect B5, wherein the hydrophilic monomer is selected from vinyl pyrrolidone and N-vinyl caprolactam.

Aspect B7. The sorbent of any of aspects B5-B6, wherein the hydrophobic monomer is selected from divinylbenzene and styrene.

Aspect B8. The sorbent of any of aspects B5-7, wherein the sorbent is selected from a strong cation exchange sorbent, a strong anion exchange sorbent, a weak cation exchange sorbent, and a weak anion exchange sorbent.

Aspect B9. The sorbent of any of aspects B1-B8, wherein the aptamers or affimers are linked to the solid support by a chemically cleavable linkage.

Aspect B10. The sorbent of any of aspects B1-B8, wherein the aptamers or affimers are linked to the solid support by an enzymatically cleavable linkage.

Aspect B11. The sorbent of aspect B10, wherein the solid support comprises an attached enzyme that is adapted to enzymatically cleave the aptamers or affimers from the solid support, thereby allowing a complex of the aptamer or affimer and the target protein to be released from the solid support for further processing.

Aspect B12. The sorbent of any of aspects B1-B11, wherein the aptamers or affimers are selected for their high affinity towards low-abundance proteins, for their high affinity towards high-abundance proteins, or both.

Aspect B13. The sorbent of any of aspects B1-B12, wherein the solid support comprises an attached enzyme that is adapted to digest the target protein after activation of the attached enzyme.

Aspect B14. The sorbent of any of aspects B1-B13, wherein the solid support comprises an attached proteolytic enzyme.

Aspect B15. The sorbent of aspect B14, wherein the proteolytic enzyme is selected from trypsin, chymotrypsin, Glu-C, Lys-C, Arg-C, Asp-N, BNPS or NCS/urea, clostripain, CNBr, CNBr (methyl-Cys), CNBr (with acids), formic acid, hydroxylamine, iodosobenzoic acid, Lys-N, neutrophil elastase, NBS, NTCB, pancreatic elastase, pepsin A, prolyl endopeptidase, proteinase K, staphylococcal peptidase thermolysin, and combinations thereof.

Aspect B16. The sorbent of any of aspects B14-B15, wherein the proteolytic enzyme is attached to the solid support through a flexible linker Aspect B17. The sorbent of any of aspects B14-B15, wherein the proteolytic enzyme is attached to the solid support through a cleavable linker.

Aspect B18. The sorbent of any of aspects B14-B15, wherein the proteolytic enzyme is attached to the solid support through an enzymatically cleavable linker.

Aspect B19. The sorbent of any of aspects B14-B15, wherein the proteolytic enzyme is attached to the sorbent through a chemically cleavable linker.

Aspect B20. The sorbent of aspect B19, wherein the chemically cleavable linker is selected from chemical linkers that are cleaved upon exposure to nucleophilic and/or basic conditions, chemical linkers that are cleaved upon exposure to electrophilic and/or acidic conditions, chemical linkers that are cleaved upon exposure to reducing conditions, chemical linkers that can be cleaved upon exposure to oxidizing conditions, hydroxylamine cleavable linkers, chemical linkers containing bis-succimide esters, chemical linkers containing bis acylazides, and chemical linkers containing maleimides.

Aspect B21. The sorbent of any of aspects B14-B20, wherein the proteolytic enzyme is chemically activated with a change in pH.

Aspect B22. The sorbent of any of aspects B14-B20, wherein the proteolytic enzyme is thermally activated by heating or cooling.

Aspect B23. The sorbent of any of aspects B1-B22, wherein the sorbent is disposed in a multi-well strip, a multi-well plate, a column, a single-use cartridge, or an ELISA plate.

Aspect B24. A kit comprising a sorbent in accordance with any of aspects B1-B23, and one or more kit components selected from (a) a washing solution that comprises a surfactant and a salt, (b) a pretreatment solution, (c) one or more elution solutions (d) one or more proteolytic enzyme solutions, (e) a collection plate, (f) a cap mat, (g) calibration and reference standards, and (h) instructions for use.

EXAMPLES

Example 1. Immobilization of Aptamer Using Reductive Amination

Example 1A. Particle Activation with Aldehydic Silane

Inorganic-organic 5 μm BEH300 particles are made following the procedure reported in Wyndham et al. WO 2008/103423. A slurry is prepared by adding 1.0 g of 5 μm BEH300 (Waters Corporation, Milford Mass., USA, specific surface area (SSA) 80 $m^2/g$, total pore volume (TPV) 0.8 cc/g, Average pore diameter (APD) 300 Å) into a 50 mL round bottom flask equipped with a magnetic stir bar mixed with approximately 5 mL of 50 mM ammonium Bicarbonate (Sigma Aldrich, St. Louis, Mo., USA) pH 9.0 buffer. To this suspension, 220 μL of triethoxysilylbutyraldehyde (Gelest, Morrisville, Pa., USA) pre-dissolved in 5 mL of ethanol is added to the flask and the mixture allowed to stir (300 rpm) for 2 h at room temperature. The mixture is then transferred into a 50 mL centrifuge tube. The particles are washed three times (10 mg/mL buffer) via centrifugation (4500 rpm) to remove unreacted silane and two times with ethanol and stored at 4° C. before use. This approach is appropriate for preparing materials with aldehyde bonding coverage between 1.4-3 umole per $m^2$. The coverage is easily tuned by the amount of silane added in the reaction. Carbon content may be determined by combustion analysis, and particle morphology may be determined by SEM.

Example 1B. Immobilization of Aptamer on Aldehydic Modified Particles

Immobilization of aptamer on aldehyde activated particle is carried out using the reductive amination. A suspension is prepared by adding 0.6 g of materials from Example 1A in a 50 mL flask equipped with a magnetic bar and slurried with 5 mL, 50 mM ammonium bicarbonate pH 9 buffer. To this suspension, 16 mg of Aptamer pre-dissolved in 13 mL, 50 mM ammonium bicarbonate pH 9 buffer is added, followed by addition of 2 mL of coupling solution (containing 1 M NaCNBH$_3$ (Sigma Aldrich) in 50 mM ammonium bicarbonate pH 9 buffer). The mixture is left for 2 h at room temperature with continued stirring at 300 rpm. The reaction is quenched by adding 2 mL of 1 M ethanolamine (Sigma Aldrich) in buffer and left stirring for an extra 30 min at room temperature. Particles are washed four times with 50 mM ammonium bicarbonate pH 9 buffer with 10 minutes shaking to remove excess of aptamer and ethanolamine (Acros Organics, Morris Plains, N.J., USA). Particles are washed with pH 4 Trifluoroacetic acid (Sigma Aldrich once and stored in this solvent at 4° C. prior use.

Example 1C. Immobilization of a Mixture of Aptamer and Trypsin

Immobilization of the aptamer and trypsin is carried out using reductive amination of aldehyde activation particles. 0.6 g of aldehyde activated BEH particles from Example 1A are added into a 50 mL flask equipped with a magnetic bar and slurried with 5 mL of 50 mM ammonium bicarbonate pH 9 buffer. A mixture of 8 mg of Aptamer and 8 mg of trypsin (using the acid stable trypsin) mixed with benzamidine pre-dissolved in 13 mL of 50 mM ammonium bicarbonate pH 9 buffer is added to the particle solution, followed by addition of 2 mL of coupling solution (containing 1 M NaCNBH$_3$ 50 mM ammonium bicarbonate pH 9 buffer). The reaction mixture is left stirring for 2 hr at room temperature. The reaction is quenched by adding 2 mL of 1 M ethanolamine (Acros Organics) in buffer and the left stirring for 30 min at room temperature. Particles are washed with centrifugation four times with 50 mM ammonium bicarbonate pH 9 buffer with 10 minutes shaking to remove excess of aptamer, trypsin and ethanolamine.

Example 1D. Sequential Immobilization of Aptamer and Trypsin

Immobilization of aptamer on aldehyde activated particle is carried out using the reductive amination as described in Example 1B with less aptamer to allow for immobilization of trypsin on the same solid support. A suspension is prepared by adding 0.6 g of materials from Example 1A in a 50 mL flask equipped with a magnetic bar and slurried with 5 mL, 50 mM ammonium bicarbonate pH 9 buffer. To this suspension, 8 mg of Aptamer pre-dissolved in 13 mL, 50 mM ammonium bicarbonate pH 9 buffer is added, followed by addition of 2 mL of coupling solution (containing 1 M NaCNBH$_3$ (Sigma Aldrich) in 50 mM ammonium bicarbonate pH 9 buffer). The mixture is left for 2 h at room temperature with continued stirring at 300 rpm. Particles are washed four times with 50 mM ammonium bicarbonate pH 9 buffer with 10 minutes shaking to remove excess of aptamer. The particles are redispersed in 5 ml 50 mM ammonium bicarbonate pH 9 buffer and transferred into a 50 mL flask equipped with a magnetic bar for trypsin immobilization. 40 mg of trypsin with appropriate amount of benzamidine (3 g of benzamidine for 1 mg trypsin) pre-dissolved in 13 mL of 50 mM ammonium bicarbonate pH 9 buffer is added to the suspension, followed by addition of 2 mL of coupling solution (containing 1 M NaCNBH$_3$ 50 mM ammonium bicarbonate pH 9 buffer). Reaction is left stirring for 2 hr at room temperature. The reaction is quenched by adding 2 mL of 1 M ethanolamine (Acros Organics) in buffer and the left stirring for 30 min at room temperature. Particles are transferred into a 50 mL centrifuge tube. Particles are washed by centrifugation four times with 50 mM ammonium bicarbonate pH 9 buffer with 10 minutes shaking to remove excess of trypsin and ethanolamine. The particles are stored as a slurry in pH4 water at 4° C. prior to use.

Example 2. Immobilization Using a Streptavidin/Biotin Activated Support

Example 2A. Activation of an Aldehydic Support with Streptavidin

Streptavidin is bound to the aldehyde particles Example 1A, where 1.0 g of 3.5 μm BEH600 (Waters Corporation, Milford Mass., specific surface area (SSA) 40 m$^2$/g, total pore volume (TPV) 0.6 cc/g, Average pore diameter (APD) 600 Å) are used instead of the BEH300, through reductive amination. A suspension is prepared by adding 0.6 g aldehyde activated particles into a 100 mL flask equipped with a magnetic bar and slurried with 50 mM ammonium bicarbonate pH 9 buffer. In a separate flask, a solution of streptavidin is prepared by dissolving 8 mg of streptavidin at a concentration of 10 mg/mL in 50 mM ammonium bicarbonate pH 9. The streptavidin solution is added into the particle suspension followed by addition of 2 mL of coupling solution (containing 1 M NaCNBH$_3$ 50 mM ammonium bicarbonate pH 9 buffer) and the sample is mixed at room temperature for 2 hours. The reaction is quenched by adding 2 mL of 1 M ethanolamine (Acros Organics) in buffer and left stirring for 30 min at room temperature. The streptavidin activated particles are washed 4-times with buffer and centrifugation to remove unreacted streptavidin.

To these streptavidin-activated particles, any biotinylated linker or protein can be bound using streptavidin-biotin protocols, that involves mixing the activate particles with biotinylated reagents in a buffer such as 50 mM ammonium bicarbonate pH 9 for an hour at room temperature. The particles are then washed several times with buffer. The biotinylated linkers may include those with cleavable linkers or biotinylated aptamers.

Example 2B. Immobilization of Mixed Enzyme and Streptavidin Onto an Activated Support Immobilization of acid stable trypsin on aldehyde activated particle is carried out using reductive amination. A suspension is prepared by adding 0.6 g of materials from Example 1A in a 50 mL flask equipped with a magnetic bar and slurried with 10 mL, 50 mM ammonium bicarbonate pH 9 buffer. To this suspension 8 mg of trypsin with appropriate amount of benzamidine (3 g of benzamidine for 1 mg trypsin) pre-dissolved in 13 mL of 50 mM ammonium bicarbonate pH 9 buffer is added, followed by addition of 2 mL of coupling solution (containing 1 M NaCNBH$_3$ 50 mM ammonium bicarbonate pH 9 buffer). The reaction mixture is left stirring for 2 hr at room temperature. Particles are transferred into a 50 mL centrifuge tube. Particles are washed by centrifugation four times with 50 mM ammonium bicarbonate pH 9 buffer with 10 minutes shaking to remove excess of trypsin. A sample is taken to analyze the amount of immobilized trypsin. The rest of the sample is redispersed in appropriate buffer and the streptavidin is immobilized on using the protocols described in Example 2A. The resulting material can be used to bind any biotinylated reagents including biotinylated aptamers following the protocol described in Example 2A.

Example 2C. Immobilization of Aptamer with a Cleavable Linker Using the Streptavidin-Biotin System Immobilization of aptamer with a cleavable linker using the streptavidin-biotin complex is carried out as follows. Streptavidin activated particles from Example 2A are reacted with commercially available NHS—SS-biotin (Thermo scientific) following the protocol of reacting streptavidin activated particles with biotin described on Example 2A. A suspension is prepared with 0.6 g of streptavidin-biotin-SS—NHS ester activated particles in 50 mL of 100 mM sodium phosphate buffer pH 9 in a 100 mL flask. In a separate flask an aptamer solution is prepared by dissolving 8 mg of aptamer in 10 mL of 100 mM sodium phosphate buffer pH 9. The aptamer solution is added to the particle suspension and left to react for 1 h. The NHS ester end of the biotin reacts with any primary amine on the aptamer or affirmer or any protein. The particles are washed four times with buffer with 10 minutes between wash followed by centrifugation to remove the unreacted aptamer. The particles are then rinsed with TFA pH 4 water and refrigerated.

Example 2D. Aptamer and Cleavable Enzyme

Immobilization of a mixture of aptamer and streptavidin on aldehydic modified particles will now be described. Immobilization of aptamer and streptavidin is carried out using reductive amination of aldehyde-activated particles. 0.6 g of aldehyde-activated BEH particles of Example 1A are added into a 100 mL flask equipped with a magnetic bar and slurried with 50 mL of 50 mM ammonium bicarbonate pH 9 buffer. A mixture of 8 mg of aptamer and 8 mg of streptavidin predissolved in 13 mL of 50 mM ammonium bicarbonate pH 9 buffer is added to the particle solution, followed by addition of 2 mL of coupling solution (containing 1 M NaCNBH$_3$ 50 mM ammonium bicarbonate pH 9 buffer). The reaction is left stirring for 2 hr at room temperature and is quenched by adding 2 mL of 1 M ethanolamine in buffer and then left stirring for 30 min at room temperature. Particles are washed four times with 50 mM ammonium bicarbonate pH 9 buffer with 10 minutes shaking to remove excess of aptamer, streptavidin and ethanolamine. To these particles a sulfo NHS—SS biotinylated reagent is added and attached to the streptavidin using the procedure described in Example 2C. A protease enzyme such as the trypsin can be bound to this support using the cleavable NHS ester on the biotin. A suspension is prepared using the 0.6 g of particles with mixed aptamer and a sulfo NHS—SS-biotinylated streptavidin with 100 mL 50 mM sodium phosphate buffer pH 9. To this particle suspension, 8 mg of trypsin pre-dissolved in 10 mL 100 mM sodium phosphate buffer pH 9 with added appropriate amount of benzamidine and allowed to react at room temperature for 1 h. The particles are then transferred to 50 mL centrifuge tube, washed 4 times with buffer and centrifugation to remove unreacted enzyme. The particles are then rinse with TFA pH 4 water and refrigerated.

Example 3A. Immobilization of the Aptamer on Amine Modified Particles

Particle activation with amino silane will now be described. A suspension of 10.0 g of BEH particles (Waters Corporation, Milford, Mass.) is prepared by adding the particles to a 250 mL round bottom flask and dispersing the particles in toluene (150 mL, Fisher Scientific, Hampton, N.H.) the mixture is dried with a dean stark trap at 110° C. for 2 h under nitrogen atmosphere. The mixture is then cooled down to 40° C. before addition of 1 mL of neat aminopropyltrimethoxy silane (Gelest). The reaction mixture is mixed for 10 minutes before heating 70° C. for 2 hours, after which the reaction is cooled down. The aminated particles are washed on 0.5 μm Tyvek and washed twice with 50% ethanol in water and twice with ethanol (Fisher Scientific). Amine modified particles are dried at 80° C. under vacuum for 16 hours. The particles are analyzed for CHN for calculation of coverage and SEM for particle morphology.

Example 3B. Attaching the Aptamer Through a Cleavable Linker

A cleavable linker such as Bis[2-(succinimidooxycarbonyloxy)ethyl]sulfone (BSOCOES) is NHS ester biofunctional linker that can be used to bond the aptamer to amine activated particles. A stock solution is prepared by dissolving BSOCOES in DMF to be used to activate the amine particles. A suspension is prepared with the 0.6 g of amine modified particles in 50 mL of 100 mM sodium phosphate buffer pH 8. To this suspension BSOCOES predissolved in DMF is added and allowed to react for then 8 mg of predissolved aptamer (10 mg/ml) in 100 mM sodium phosphate buffer is added to the suspension and allowed to react for 1 h at room temperature. The particles are then washed 4 times with buffer and centrifugation. After wash the particles are rinsed with pH 4 TFA water and left in the fridge.

Example 4. Depletion of High-Abundance Human Serum Albumin (HSA)

A plasma sample is treated with an agent that disrupts protein-protein interaction such as disodium EDTA, formic acid, TCA, acetic acid, TFA, phosphoric acid, or NH$_4$OH.

The resulting treated plasma sample, with or without neutralization, is added to a sorbent bed, which contains solid support particles (e.g., BEH particles) having a molar excess of chemically linked HSA affinity reagent, such as aptamers or affirmers targeting HSA. A contact time and flow rate sufficient for proper diffusion kinetics and binding of HSA to the affinity reagents is established.

The following steps may then be used in combination or alone: (a) a low stringency wash is performed with a low power surfactant and moderate salt concentration to disrupt any low Kd protein-protein interactions between HSA and plasma proteins and/or (b) a high stringency wash is performed with a solution that contains a powerful surfactant and chaotropic salt to disrupt any non-specific binding to disrupt interactions that have a Kd above the nM Kd interactions between the affinity reagent and the target HSA.

The eluate from the low and/or high stringency washes is collected. Surfactant and salt are then removed and the eluate concentrated by passing the eluate through an appropriate solid phase extraction (SPE) device, such as an Oasis® HLB, Oasis® PRIME HLB, Oasis® MCX, or Oasis® MAX sorbent device available from Waters Corporation, Milford, Mass., USA. The resulting clean, concentrated eluate may be used downstream for protein quantitation.

Example 5. Enrichment of Low-Abundance Thyroglobulin from Plasma

A plasma sample is added directly to an affinity sorbent bed, which contains solid support particles having a molar excess of chemically linked thyroglobulin affinity reagent, such as aptamers or affimers targeting thyroglobulin. Multiple affinity reagents may be attached to the sorbent to enrich multiple targets simultaneously.

A high stringency wash is performed with a solution that contains a powerful surfactant and chaotropic salt to disrupt any non-specific binding to disrupt interactions that have a Kd above the $10^{-8}$M Kd interactions between the affinity reagent and the target thyroglobulin. The wash is discarded.

The bound thyroglobulin is then digested with a proteolytic enzyme, such as trypsin or Lys-C, which may be either chemically linked to the sorbent or added to the sorbent bed as part of a digestion reagent mix. Where the proteolytic enzyme is chemically linked, a linker of suitable length may be employed to enhance the ability of the enzyme to reach and digest bound protein. The proteolytic enzyme may be activated, for example, by temperature elevation or by establishing a particular pH.

The digested protein mix is then eluted with a suitable elution solution, such as a buffer, which may have neutralizing properties, and the eluate may then be used for downstream protein quantitation.

The invention claimed is:

1. A method of sample treatment comprising:
adding a sample fluid comprising a sample that comprises, or potentially comprises, at least one target protein to a sorbent, the target protein being a low-abundance protein, the sorbent comprising a solid support with at least one attached high affinity reagent that has a specific high affinity for the target protein, thereby resulting in sorbent with bound target protein;
adding a washing solution that comprises a surfactant and a salt to the sorbent, thereby removing substances for which the at least one high affinity reagent does not have a specific affinity including said substances that are indirectly bound to the sorbent by attachment to the target protein;
wherein the low-abundance protein is digested into fragments while hound to the sorbent and the fragments are eluted.

2. The method of claim 1, wherein the sample fluid is prepared by combining the sample with a pretreatment solution that disrupts protein binding.

3. The method of claim 2, wherein the pretreatment solution comprises an aqueous acidic or basic solution.

4. The method of claim 1, (a) wherein the target protein is digested by adding a solution comprising a proteolytic enzyme to the sorbent, (b) wherein the sorbent comprises an attached proteolytic enzyme and wherein the low-abundance protein is digested into fragments by activating the proteolytic enzyme, or (c) wherein the sorbent comprises an attached cleavable enzyme and wherein the low-abundance protein is digested into fragments by a process that comprises chemically cleaving the attached cleavable enzyme and releasing a proteolytic enzyme.

5. A method of sample treatment comprising:
adding a sample fluid comprising a sample that comprises, or potentially comprises, at least one target protein to a sorbent, the target protein being a low-abundance protein, the sorbent comprising a solid support with at least one attached high affinity reagent that has a specific high affinity for the target protein, thereby resulting in sorbent with bound target protein;
adding a washing solution that comprises a surfactant and a salt to the sorbent, thereby removing substances for which the at least one high affinity reagent does not have a specific affinity including said substances that are indirectly bound to the sorbent by attachment to the target protein; and
adding an elution solution to the sorbent, thereby removing the low-abundance protein from the sorbent;
(a) wherein the high affinity reagent is linked to the support by an enzymatically cleavable linkage and wherein the elution solution comprises an enzyme that cleaves the enzymatically cleavable linkage or (b) wherein the high affinity reagent is linked to the support by linkage that is cleaved upon exposure to nucleophilic and/or basic conditions, upon exposure to electrophilic and/or acidic conditions, or upon exposure to reducing conditions, and wherein the sorbent is exposed to an eluting solution that establishes such conditions thus cleaving a complex of the high affinity reagent with bound target protein.

6. The method of claim 1, wherein the high affinity reagent is an aptamer or an affimer.

7. The method of claim 1, wherein the sample is selected from a whole blood sample, a plasma sample, and a serum sample.

8. The method of claim 1, wherein the low-abundance protein is selected from cruloplasmin, complement factors C4, C9, C8, and C5, IgD, C1 inhibitor, RBP, iC3b, throxoin binding Globulin, complement proteins, thrombis precursor protein, C-reactive protein, Bb fragment, ferritin, randes, SC5b-9 complex, myoglobin, thryoglobulin, TPA (tissue plasminogen activator), neuron specific enolase, C-peptide, alpha-fetoprotein, TNF-binding proteins, PSA (prostate specific antigen), prostatic acid phosphatase, CEA (carcinoembryonic antigen), myelin basic protein, troponin I, interleukins, MIP_1 alpha, tissue factor, GCSF (granulocyte-colony stimulating factor), interferons, and combinations thereof.

9. The method of claim 2, wherein the pretreatment solution is selected from an aqueous $H_3PO_4$ solution, an aqueous $NH_4OH$ solution, an aqueous ethylenediaminetetraacetic acid (EDTA) solution, an aqueous formic acid solution, an aqueous acetic acid solution, an aqueous trichloroacetic acid (TCA) solution, and an aqueous trifluoroacetic acid (TFA) solution.

10. The method of claim 5, wherein the sample fluid is prepared by combining the sample with a pretreatment solution that disrupts protein binding.

11. The method of claim 10, wherein the pretreatment solution comprises an aqueous acidic or basic solution.

12. The method of claim 10, wherein the pretreatment solution is selected from an aqueous $H_3PO_4$ solution, an aqueous $NH_4OH$ solution, an aqueous ethylenediaminetetraacetic acid (EDTA) solution, an aqueous formic acid solution, an aqueous acetic acid solution, an aqueous trichloroacetic acid (TCA) solution, and an aqueous trifluoroacetic acid (TFA) solution.

13. The method of claim 5, wherein the high affinity reagent is an aptamer or an affimer.

14. The method of claim 5, wherein the sample is selected from a whole blood sample, a plasma sample, and a serum sample.

15. The method of claim 5, wherein the low-abundance protein is selected from cruloplasmin, complement factors C4, C9, C8, and C5, IgD, C1 inhibitor, RBP, iC3b, throxoin binding Globulin, complement proteins, thrombis precursor protein, C-reactive protein, Bb fragment, ferritin, randes, SC5b-9 complex, myoglobin, thryoglobulin, TPA (tissue plasminogen activator), neuron specific enolase, C-peptide, alpha-fetoprotein, TNF-binding proteins, PSA (prostate specific antigen), prostatic acid phosphatase, CEA (carcinoembryonic antigen), myelin basic protein, troponin I, interleukins, MIP_1 alpha, tissue factor, GCSF (granulocyte-colony stimulating factor), interferons, and combinations thereof.

16. The method of claim 5, wherein the high affinity reagent is linked to the support by an enzymatically cleavable linkage, and wherein the elution solution comprises an enzyme that cleaves the enzymatically cleavable linkage.

17. The method of claim 5, wherein the high affinity reagent is linked to the support by linkage that is cleaved upon exposure to nucleophilic and/or basic conditions, and wherein the sorbent is exposed to an eluting solution that establishes said conditions thus cleaving a complex of the high affinity reagent with bound target protein.

18. The method of claim 5, wherein the high affinity reagent is linked to the support by linkage that is cleaved upon exposure to electrophilic and/or acidic conditions, and wherein the sorbent is exposed to an eluting solution that establishes said conditions thus cleaving a complex of the high affinity reagent with bound target protein.

19. The method of claim 5, wherein the high affinity reagent is linked to the support by linkage that is cleaved upon exposure to reducing conditions, and wherein the sorbent is exposed to an eluting solution that establishes said conditions thus cleaving a complex of the high affinity reagent with bound target protein.

* * * * *